United States Patent [19]

Mikami

[11] Patent Number: 5,726,330
[45] Date of Patent: Mar. 10, 1998

[54] HIGHLY CRYSTALLINE 22-OXAVITAMIN D DERIVATIVES

[75] Inventor: Tetsuhiro Mikami, Tokyo, Japan

[73] Assignee: Chugai Seiyaku Kabushiki Kaisha, Tokyo, Japan

[21] Appl. No.: 416,857

[22] PCT Filed: Oct. 18, 1993

[86] PCT No.: PCT/JP93/01490

§ 371 Date: Apr. 17, 1995

§ 102(e) Date: Apr. 17, 1995

[87] PCT Pub. No.: WO94/08958

PCT Pub. Date: Apr. 28, 1994

[30] Foreign Application Priority Data

Oct. 16, 1992 [JP] Japan .................. 4-321100

[51] Int. Cl.⁶ .................. C07C 401/00
[52] U.S. Cl. .................. 552/653
[58] Field of Search .................. 552/653

[56] References Cited

U.S. PATENT DOCUMENTS

| | | | |
|---|---|---|---|
| 5,089,641 | 2/1992 | DeLuca | 552/653 |
| 5,200,536 | 4/1993 | Ikekawa et al. | 552/653 |
| 5,292,728 | 3/1994 | Neef et al. | 514/167 |
| 5,378,695 | 1/1995 | Calverley et al. | 514/167 |
| 5,411,949 | 5/1995 | Neef et al. | 514/167 |

FOREIGN PATENT DOCUMENTS

| | | |
|---|---|---|
| 0184112 | 6/1986 | European Pat. Off. |
| 9009992 | 9/1990 | WIPO |

OTHER PUBLICATIONS

A. Brown et al. *Kidney International* (Supplement 29), vol. 38, 1990, pp. S-22-S-27.
N. Kubodera et al, *Chemical and Pharmaceutical Bulletin*, vol. 40, No. 6, Jun. 1992, pp. 1494-1499.
Morrison & Boyd, *Organic Chemistry*, 4th ed. (1983), pp. 830-836.
Greene, *Protective Groups in Organic Synthesis* 2nd ed., 1991, pp. 10-14, 77-83 & 88-92.

*Primary Examiner*—Richard L. Raymond
*Attorney, Agent, or Firm*—Browdy and Neimark

[57] ABSTRACT

Highly crystalline vitamin D derivatives are represented by the formula:

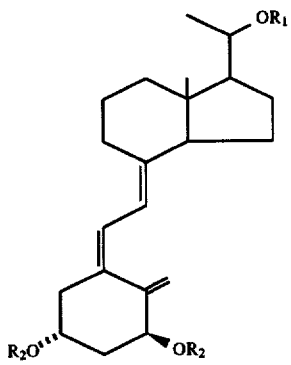

(where $R_1$ is a straight or branched $C_4$–$C_9$ alkyl group optionally having a hydroxyl group; $R_2$ and $R_3$ which may be the same or different are each an acyl group). 22-oxavitamin D derivatives of high purity are produced by hydrolyzing said compounds which derivatives are useful as pharmaceuticals.

9 Claims, No Drawings

HIGHLY CRYSTALLINE 22-OXAVITAMIN D DERIVATIVES

FIELD OF THE INVENTION

This invention relates to a process for producing 22-oxavitamin D derivatives that have the potential for use as pharmaceuticals. The invention also relates to highly crystalline 22-oxavitamin D derivatives produced by that process.

BACKGROUND OF THE INVENTION

Heretofore, 22-oxavitamin D derivatives have been produced by several methods, one of which is described in Japanese Laid-open Patent Publication No. 61-267550. However, the 22-oxavitamin D derivatives produced by the conventional methods have the disadvantage that their crystallinity is low enough to cause variations in purity. This defect is inherent in 22-oxavitamin D derivatives and absent from the manufacture of ordinary vitamin D derivatives.

SUMMARY OF THE INVENTION

An object, therefore, of the invention is to provide novel vitamin D derivatives having high crystallinity.

Another object of the invention is to provide a process that overcomes the aforementioned drawback of the prior art to enable the production of highly pure 22-oxavitamin D derivatives.

The present inventors conducted intensive studies with a view to attaining these objects and found that 22-oxavitamin D derivatives having the hydroxy group in 1- and 3-positions protected with an acyl group had high crystallinity and that 22-oxavitamin $D_3$ derivatives produced by hydrolyzing those compounds had a very high purity.

Thus, in its first aspect, the present invention relates to novel 22-oxavitamin D derivatives represented by the general formula (I):

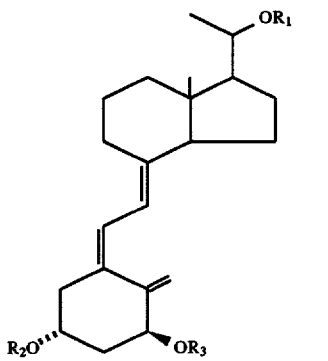

where $R_1$ is a straight or branched $C_4$–$C_9$ alkyl group optionally having a hydroxyl group; $R_2$ and $R_3$ which may be the same or different are each an acyl group.

In its second aspect, the invention relates to a process in which the compounds defined above are hydrolyzed to produce 22-oxavitamin $D_3$ derivatives represented by the general formula (II):

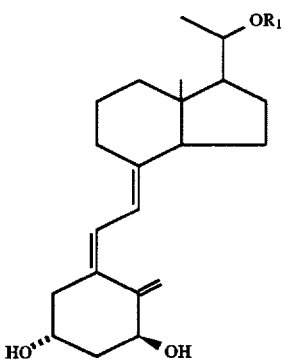

where $R_1$ is a straight or branched $C_4$–$C_9$ alkyl group optionally having a hydroxyl group.

The compounds represented by the general formula (I) include but are not limited to:

1α,3β-diacetyloxy-20S-(3-hydroxy-3-methylbutyloxy)-9,10-secopregna-5,7,10(19)-triene;

1α,3β-dipropionyloxy-20S-(3-hydroxy-3-methylbutyloxy)-9,10-secopregna-5,7,10(19)-triene;

1α,3β-dibutyryloxy-20S-(3-hydroxy-3-methylbutyloxy)-9,10-secopregna-5,7,10(19)-triene; and 1α,3β-dibenzoyloxy-20S-(3-hydroxy-3-methylbutyloxy)-9,10-secopregna-5,7,10(19)-triene.

The invention embraces the crystals of these compounds. The crystals may be separated by conventional procedures such as column chromatography and high-performance liquid chromatography, followed by recrystallization from appropriate solvents such as n-hexane. Thus, the invention provides 1α,3β-diacetyloxy-20S-(3-hydroxy-3-methylbutyloxy)-9,10-secopregna-5,7,10(19)-triene in the form of a crystal of X-ray diffraction compatible quality.

[Best Mode for Carrying Out the Invention]

The compounds of the invention can be produced by acylating, in the usual manner, the hydroxyl group in the 1- and 3-positions of 22-oxavitamin D derivatives that are prepared typically by the method described in Japanese Laid-open Patent Publication No. 61-267550, supra.

The compounds of the invention can also be produced by acylating, in the usual manner, the 1- and 3-positions of 22-oxaprovitamin D derivatives described in the above Patent Publication, followed by irradiating the acylated derivatives with light and subjecting the thus obtained compounds to thermal isomerization reaction.

Acylation in these reaction can be performed in the usual manner by reaction with acid anhydrides or acid halides in basic solvents. Preferred basic solvents include pyridine, collidine, triethylamine, etc. Exemplary reactant acid anhydrides include acetic anhydride, propionic anhydride, butyric anhydride, benzoic anhydride, etc. Exemplary reactant acid halides include acetyl chloride, propionyl chloride, butyryl chloride, benzoyl chloride, etc.

Hydrolysis for producing the compounds of the general formula (II) is performed in solvents under basic conditions using alkali metal hydroxides. Any inert solvents may be used and preferred examples are alcoholic solvents such as methanol and ethanol. Exemplary alkali metal hydroxides include lithium hydroxide, sodium hydroxide, potassium hydroxide, etc; these hydroxides are used as aqueous solutions containing them at suitable concentrations.

The following examples are provided for the purpose of further illustrating the invention but are in no way to be taken as limiting.

EXAMPLE 1

Process for Producing 1α,3β-Diacetyloxy-20S-(3-Hydroxy-3-Methylbutyloxy)-9,10-Secopregna-5,7,10(19)-Triene and the Crystal Thereof 1α,3β-Dihydroxy-20S-(3-hydroxy-3-methylbutyloxy)-9,10-secopregna-5,7,10(19)-triene (4.81 g) was dissolved in pyridine (24 ml) and, after adding acetic anhydride (3.2 ml), the mixture was stirred at room temperature for 2 days. The reaction solution was added to ice water (50 ml) and subjected to extraction with hexane (120 ml). The extract was washed twice with 5% HCl (50 ml), then with saturated aqueous sodium hydrogen carbonate (50 ml) and saturated brine (50 ml), followed by drying with anhydrous magnesium sulfate. The desiccant was filtered off and the solvent was distilled off under vacuum to produce a crude crystal (4.19 g). Recrystallization from distilled hexane (24 ml) gave the titled compound in an amount of 4.12 g (yield, 71%).

m.p.: 88°–89° C.

X-ray diffraction (crystallographic data):

a=16.3591(8)Å; b=6.9304(5)Å; c=14.1352(8)Å;

β=71.499(4)Å; V=1519.7Å$^3$; space group: P2$_1$ (monoclinic):

z=2; D(cal'd)=1.098 g/cm$^3$;

Linear Absorption Coefficient: 5.675 cm$^{-1}$ [μ(CuKα)]

UV(EtOH): $\lambda_{max}$=249.8 nm, λ=266.8, 210.9

IR(KBr)cm$^{-1}$: 3504.07, 2971.80, 2933.23, 1739.50, 1380.80, 1224.59, 1151.31, 1083.81, 962.32

$^1$H-NMR(CDCl$_3$)δ: 5.478(H-1,d—d: J1,2α=3.96; J1,2β= 6.27), 2.07(H-2α: m), 1.99(H-2β: m), 5.175(H-3d: J2a,3= 3.96; J2b,3=8.25; J2a,3=3.96; J2b,3=8.25), 2.643(H-4α,m: J3,4a=3.96; J3,4b=7.92; J4a,4b=13.20), 2.361(H-4β,m), 6.338(H-6,d: J6,7=11.22), 5.930(H-7,d: J6,7=11.22), 1.93 (H-9α,m), 1.51(H-11,m), 1.89(H-12β,m: J11,12'=3.60; 11', 12'=12.53; 12,12'=12.53), 1.31(H-12α, m; J111,12'=3.60; 11'12'=12.53; 12,12'=12.53), 1.76(H-14,m), 2.817(H-15α, m), 1.68(H-15β,m: J14,15α=3.30; J15α,15β=11.21), 1.68 (H-16β,m), 1.54(H-16α,m), 1.53(H-17,m), 0.512(H-18,s), 5.321(H-19αd: J=0.32), 5.037(H-19β,d: J=0.32), 3.245(H-20,m: J17,20=7.59; J20,21=5.94), 1.189(H-21,d: J20,21= 5.94), 3.835(H-23,m), 3.480(H-23,m: J23,24=5.94; J23,23= 9.24), 1.733(H-24,d—d: J23,24=5.60), 1.232(H-26 and H-27,s), 2.047(H-Ac-Me,s), 2.031(H-Ac-Me,s)

$^{13}$C-NMR(CDCl$_3$)δ: 12.453(C18), 18.886(C21), 22.102 (C11), 21.132(Ac-Me), 21.275(Ac-Me), 23.234(C16), 25.732(C9), 28.984(C15), 29.110(C26 or C27), 29.290(C26 or C27), 36.873(C2), 39.550(C12), 41.527(C4), 41.563 (C24), 44.815(C13), 56.046(C14), 57.088(C17), 65.569 (C23), 69.379(C3), 70.385(C25), 72.757(C1), 78.795(C20), 115.110(C19), 117.392(C7), 124.993(C6), 131.893(C10), 142.172(C5), 142.621(C8), 169.844(Ac-CO), 170.419(Ac-CO)

| Elemental analysis (%): | | C | H | O |
|---|---|---|---|---|
| C$_{30}$H$_{46}$O$_6$ | Cal'd: | 71.68 | 9.22 | 19.10 |
| | Found: | 71.72 | 9.24 | 19.04 |

EXAMPLE 2

Process for Producing 1α,3β-Diacetyloxy-20S-(3-Hydroxy-3-Methylbutyloxy)-9,10-Secopregna-5,7,10(19)-Triene and the Crystal Thereof i) Process for producing 1α,3β-diacetyloxy-20S-(3-hydroxy-3-methylbutyloxy)pregna-5,7-diene 1α,3β-Dihydroxy-20S-(3-hydroxy-3-methylbutyloxy) pregna-5,7-diene (9.3 g) and dimethylaminopyridine (0.93 g) were dissolved in pyridine (46.6 ml) and acetic anhydride (4.66 ml) was added to the stirred solution at room temperature. Thirty minutes later, water (180 ml) was added and the mixture was stirred at room temperature for 30 min. The precipitated crystal was recovered by filtration and washed with water (180 ml) thoroughly. Vacuum drying the crystal at 50° C. for 3 h gave the titled compound in an amount of 10.0 g (yield, 89%).

m.p.: 81°–84° C. (recrystallized from acetonitrile)

IR(KBr)cm$^{-1}$: 3514, 3498, 3388, 2966, 2873, 1739, 1467, 1462, 1433, 1371, 1236, 1149, 1095, 1030, 970, 943, 617, 615

$^1$H-NMR(CDCl$_3$)δ: 0.60(3H,s,H-18), 1.00(3H,s,H-19), 2.04(3H,s,Ac), 2.06(3H,s,Ac), 2.3–2.7(3H,m), 3.2–3.6(2H, m), 3.7–3.9(2H,m), 4.9–5.1(2H,m), 5.4–5.7(2H,m)

ii) Process for Producing 1α,3β-Diacetyloxy-20S-(3-hydroxy-3-methylbutyloxy)-9,10-secopregna-5,7,10(19)-triene and its crystal 1α,3β-Diacetyloxy-20S-(3-hydroxy-3-methylbutyloxy) pregna-5,7-diene (230 mg) was dissolved in tetrahydrofuran (THF, 230 ml) in a photoreaction cell. The solution was irradiated with light from a 400-W high-pressure mercury lamp through a Vycor filter for 3 min in an argon atmosphere under cooling with ice. The reaction solution was transferred to another vessel as it was washed with THF (50 ml) and heated under reflux for 150 min. The reaction solution was concentrated, purified by analytical high-performance liquid chromatography (column, silica gel 60; solvent, 4:1 mixture of c-hexane and ethyl acetate) and recrystallized from n-hexane to produce the titled compound in an amount of 60 mg (yield: 26%).

The instrumental data of this compound were in agreement with those obtained in Example 1.

EXAMPLE 3

Process for Producing 1α,3β-Dihydroxy-20S-(3-Hydroxy-3-Methylbutyloxy)-9,10-Secopregna-5,7,10(19)-Triene 1α,3β-Diacetyloxy-20S-(3-hydroxy-3-methylbutyloxy)-9,10-secopregna-5,7,10(19)-triene (4.02 g) was dissolved in methanol (20 ml). After adding a methanol solution (20 ml) of 1M potassium hydroxide, the mixture was stirred for 2 h under cooling with ice. Saturated brine (100 ml) was added to the reaction solution and extraction was conducted with a mixture of ethyl acetate (200 ml) and hexane (40 ml). The extract was washed with pure water (200 ml) and saturated brine (100 ml) and then dried with anhydrous magnesium acetate. The desiccant was recovered by filtration and the solvent was distilled off under vacuum to give the titled compound (3.45 g). This compound was dissolved in ethyl acetate (33.5 ml) and hexane (77.0 ml) was added to the solution as it was heated at 35° C. under stirring. The mixture was left to cool to 25° C. over 25 h, then stirred for 6 h until it was crystallized. The crystal was recovered by filtration, washed with isopropyl ether (33.5 ml) and vacuum dried for 12 h to produce the purified crystal of the titled compound in an amount of 2.06 g (yield, 62%).

The crystal was found to have a purity of 99.6% by measurement with high-performance liquid chromatography (reverse phase on ODS; solvent, mixture of THF, water and acetonitrile).

The instrumental data of the crystal were in agreement with those listed in Japanese Laid-open Patent Publication No. 61-267550, supra.

I claim:

1. A process for producing a 22-oxavitamin $D_3$ derivative of the general formula (II):

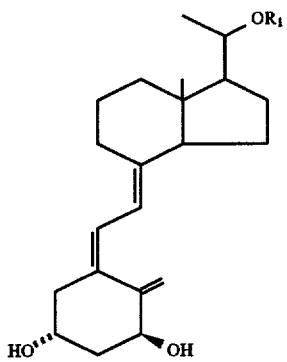

(II)

where $R_1$ is a straight or branched $C_4$–$C_9$ alkyl group optionally having a hydroxyl group by hydrolyzing a compound of the general formula (I):

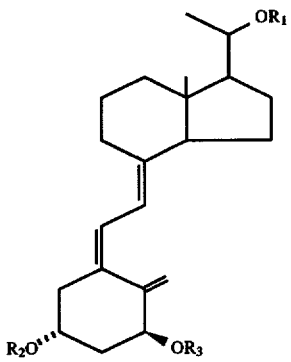

(I)

where $R_1$ is a straight or branched $C_4$–$C_9$ alkyl group optionally having a hydroxyl group; $R_2$ and $R_3$ which may be the same or different are each an acyl group.

2. A process according to claim 1 wherein the acyl group is a lower acyl group such as formyl, acetyl, propionyl or butyloyl or an aromatic acyl group such as benzoyl.

3. A process according to claim 1 wherein the acyl group is acetyl for both $R_2$ and $R_3$.

4. A compound represented by the general formula (I):

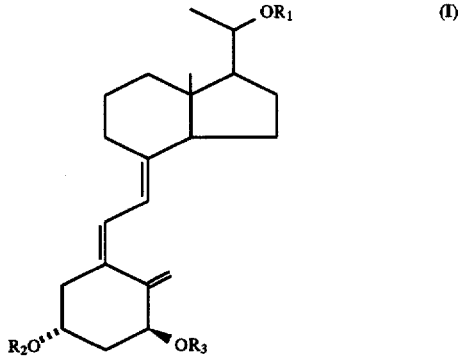

(I)

where $R_1$ is a straight or branched $C_4$–$C_9$ alkyl group optionally having a hydroxyl group; $R_2$ and $R_3$ which may be the same or different are each an acyl group.

5. A compound according to claim 4 wherein the acyl group is a lower acyl group such as formyl, acetyl, propionyl or butyloyl or an aromatic acyl group such as benzoyl.

6. A compound according to claim 4 wherein the acyl group is acetyl for both $R_2$ and $R_3$ whereas the alkyl group is 3-hydroxy-3-methylbutyl.

7. The process according to claim 1 wherein the 22-oxavitamin $D_3$ derivative is obtained in a crystalline form.

8. The process according to claim 2 wherein the 22-oxavitamin $D_3$ derivative is obtained in a crystalline form.

9. The process according to claim 3 wherein the 22-oxavitamin $D_3$ derivative is obtained in a crystalline form.

* * * * *